United States Patent
Shastri et al.

(10) Patent No.: US 8,044,196 B2
(45) Date of Patent: Oct. 25, 2011

(54) PROCESS FOR PRODUCING PURE FORM OF 2-METHYL-4-(4-METHYL-1-PIPERAZINYL)-10H-THIENO[2,3-B][1,5]BENZODIAZEPINE

(75) Inventors: Jwalant A. Shastri, Noida (IN); Akshat Bhatnagar, Noida (IN); Rajesh K. Thaper, Noida (IN); Sushil K. Dubey, Noida (IN)

(73) Assignee: Jubilant Organosys Limited, Noida (IN)

( * ) Notice: Subject to any disclaimer, the term of this patent is extended or adjusted under 35 U.S.C. 154(b) by 695 days.

(21) Appl. No.: 11/632,362

(22) PCT Filed: Jul. 14, 2004

(86) PCT No.: PCT/IN2004/000207
§ 371 (c)(1),
(2), (4) Date: Aug. 18, 2008

(87) PCT Pub. No.: WO2006/006180
PCT Pub. Date: Jan. 19, 2006

(65) Prior Publication Data
US 2009/0005556 A1   Jan. 1, 2009

(51) Int. Cl.
*C07D 243/10* (2006.01)

(52) U.S. Cl. .................................................. 540/557
(58) Field of Classification Search .................. 540/557
See application file for complete search history.

(56) References Cited

U.S. PATENT DOCUMENTS 7,425,627 B2 * 9/2008 Dolitzky et al. ............ 540/557
7,759,484 B2 * 7/2010 Dalmases Barjoan et al. ............................. 540/557

* cited by examiner

*Primary Examiner* — Brenda Coleman
(74) *Attorney, Agent, or Firm* — Blank Rome LLP

(57) ABSTRACT

Disclosed is a process for producing pure form of 2-methyl-4-(4-methyl-1-piperazinyl)-10H-thieno[2,3-b][1,5] benzodiazepine. The process comprises of reacting 2-(2-aminoanilino)-5-methylthiophene-3-carbonitrile with N-methyl piperazine in conjunction with N-methylpiperazine acid salt, to produce 2-methyl-4-(4-methyl-1-piperazinyl)-10H-thieno[2,3-b][1,5] benzodiazepine. Also disclosed is a process for obtaining the Polymorphic Form I of 2-methyl-4-(4-methyl-1-piperazinyl)-10H-thieno[2,3-b][1,5] benzodiazepine by crystallizing the crude 2-methyl-4-(4-methyl-1-piperazinyl)-10H-thieno[2,3-b][1,5] benzodiazepine in a mixture of solvents.

5 Claims, 2 Drawing Sheets

PROCESS FOR PRODUCING PURE FORM OF 2-METHYL-4-(4-METHYL-1-PIPERAZINYL)-10H-THIENO[2,3-B][1,5]BENZODIAZEPINE

This application is national stage entry under 35 U.S.C. §371 of PCT/IN04/000207, filed Jul. 14, 2004.

FIELD OF THE INVENTION

This invention in general relates to an improved process for producing an atypical neuroleptic or antipsychotic agent. More particularly, this invention provides an improved, concise and industrially feasible process for producing pure form of 2-methyl-4-(4-methyl-1-piperazinyl)-10H-thieno[2,3-b][1,5]benzodiazepine.

BACKGROUND OF THE INVENTION

2-Methyl-4-(4-methyl-1-piperazinyl)-10H-thieno[2,3-b][1,5]benzodiazepine (Olanzapine) is an atypical neuroleptic agent that has better reported efficacy and few side effects than conventional neuroleptic agents. It is useful in the treatment of psychotic patients and mild anxiety states.

U.S. Pat. No. 5,229,382 and its Continuation-In-Part application, now U.S. Pat. No. 6,008,216 to Chakrabarti, et. al., disclose processes for Olanzapine preparation by different intermediates. One of the known procedures consists of reduction and cyclization reaction of 2-(2-nitroanilino)-5-methylthiophen-3-carbonitrile with stannous chloride ($SnCl_2$) in an aqueous-alcoholic solution of hydrogen chloride followed by a reaction of thus formed 4-amino-2-methyl-10H-thieno[2,3-b][1,5]benzodiazepine [3] with N-methylpiperazine in an organic solvent or solvents mixture such as anisole, toluene, dimethylformamide or dimethylsulphoxide, preferably at a temperature from 100° to 150° C. for about 20 hrs, to which alcohol and excess water is added after the reaction is complete (Scheme A). The crude product is separated out and collected. The crude Olanzapine is then crystallized in acetonitrile and gives a crystalline form, which is designated as Form I in later patents.

In PCT applications numbered WO 02/18390 and WO 03/097650, it has been disclosed that Polymorphic Form II of Olanzapine with XRD starting from 10.26 is obtained by following the procedure disclosed in U.S. Pat. No. '382, more particularly the process disclosed in the Example 1 Sub-Example 4 for the crystallization of Olanzapine in acetonitrile,

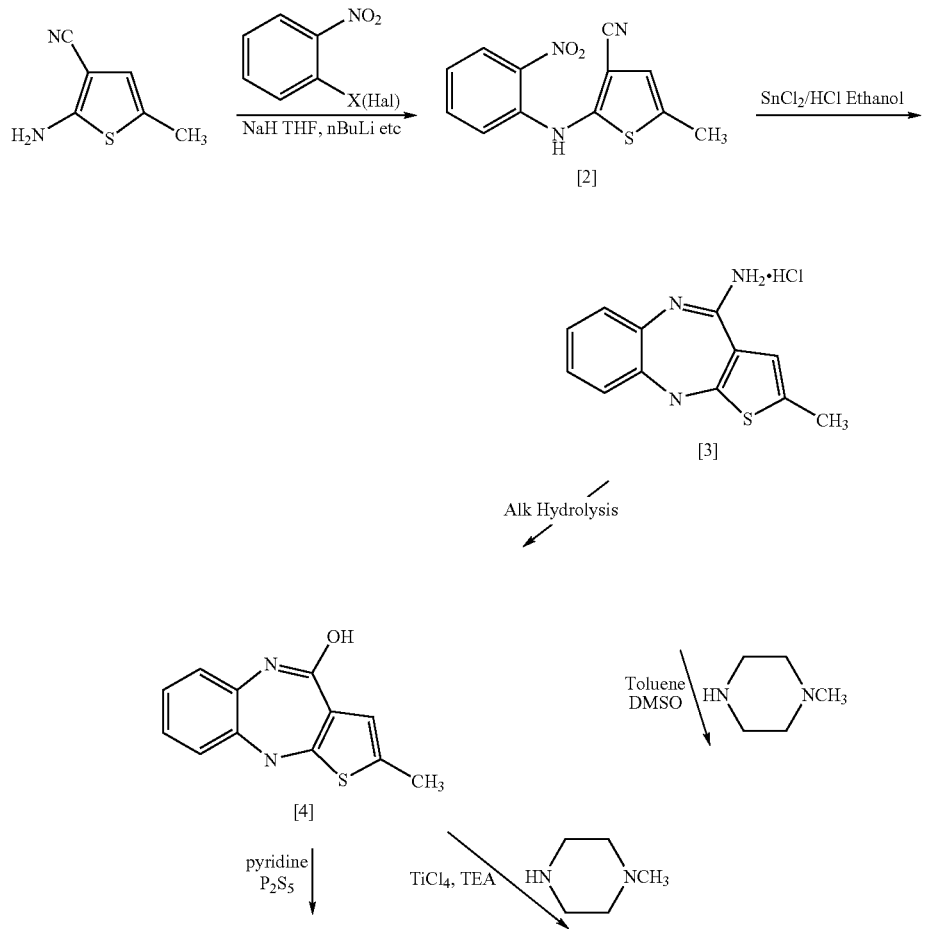

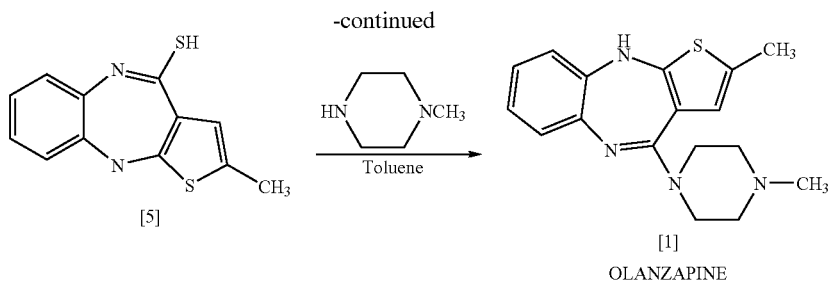

Another of the known procedure consists cyclization of 1-{[2-(2-aminoanilino)-5-methylthiophen-3-yl]carbonyl}-4-methylpiperazine (9), using titanium tetrachloride as catalyst and anisole as solvent at reflux temperature in 48 hours. The long reaction time yields multifold impurity profile and thus low productivity. The product was purified by chromatography on florisil by using ethyl acetate. The separation through chromatography is not desirable and therefore this method is not suitable for large-scale manufacturing. The product with the formula [9] is prepared in situ by reacting a compound of formula [7] with N-methyl piperazine at 100° C. in a solvent such as anisole and employing titanium chloride as a catalyst. The amino ester [7] is prepared from the reduction of corresponding nitro ester [6] e.g. by employing hydrogen and palladium/carbon in ethanol and ethyl acetate mixture or stannous chloride and hydrogen chloride in aqueous ethanol. The nitro ester can be made by condensation of thiophene with an ortho-halonitrobenzene, preferably ortho fluoro- or chloro-nitrobenzene in the presence of base, for example (a) sodium hydride in tetrahydrofuran or (b) anhydrous potassium carbonate or lithium hydroxide in dimethlysulphoxide. This reaction takes 20 hours to complete. This process is depicted in Scheme B. The reaction yields of the prior art processes are low (~30%) as all the steps take long hours to complete.

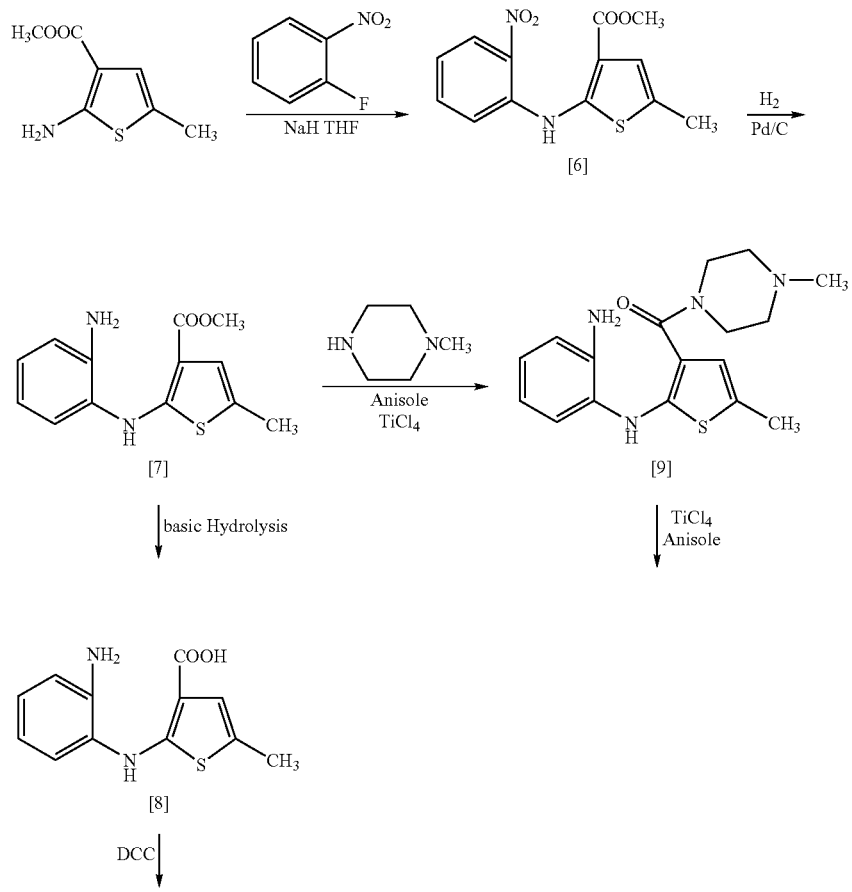

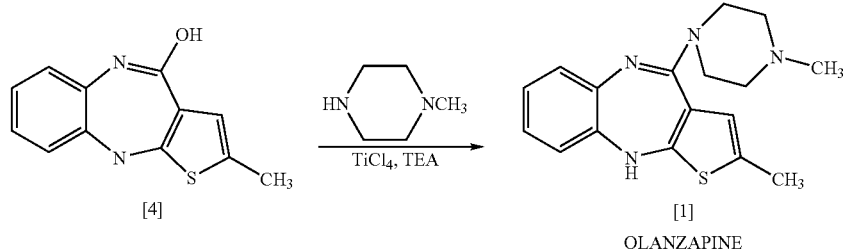

[4] → [1] OLANZAPINE

In international application no. WO 2004/00847, Olanzapine is prepared by the N-methylation of N-desmethylolanzapine with formaldehyde in presence of reducing agent e.g. borohydride of group I or II metal or of alkali metal and acetic acid in aqueous media or formic acid or by hydrogenation in presence of metal catalyst. In another process N-methylation of N-desmethylolanzapine is carried out by ethyl formate. In another process the said N-methylation is carried out by direct methylation of N-desmethylolanzapine with a methylating agent e.g. methyl iodide.

In most of the prior art methods technical grade Olanzapine is separated in the form of solvate with alcohol. Depending on the solvent used for the crystallization of technical grade Olanzapine, different polymorphic forms are obtained by different prior art methods.

Olanzapine is found in different polymorphic forms and most of the prior arts describe different conditions and solvents for the preparation of these polymorphic forms. Polymorphism can be influenced by controlling the conditions of obtaining a compound in solid form. These polymorphic forms are distinguished on the basis of IR and X-Ray diffraction data.

Attempts to reproduce the methods known in the prior art for isolation and purification of Olanzapine, obtained by the condensation of N-methylpiperazine and 4-amino-2-methyl-10H-thieno[2,3-b][1,5]benzodiazepine in organic solvent, e.g. dimethylsulphoxide and/or toluene, and subsequent addition of water and alcohol, show that obtained product contains high percentage of impurities and recovery of different solvents is difficult and thus not industrially feasible. The boiling point of dimethylsulfoxide is 189° C. The boiling point of the other solvent toluene, which is used as a co-solvent with DMSO, in most of the prior arts, is 110° C. Thus it is rather difficult to remove these solvents by conventional methods. The reaction takes 20-22 hours to complete. This long reaction time decreases the manufacturing capacity.

Other drawback of the prior art is the use of different solvents at different stages of the process. The main solvent is Dimethylsulfoxide (DMSO), which penetrates to places in the body very swiftly. Dimethylsulfoxide substitutes for water and moves rapidly through cell membranes. It has been called "water's alter ego." It changes the water structure within the cell. Thus the use of dimethyl sulfoxide is not desirable at the manufacturing level.

The present invention provides an improved process, which overcomes the drawbacks of processes recited in prior arts. The main aim of this invention is to provide a new improved and concise process for the large-scale production of Olanzapine.

Further aim of the present invention is to develop a process for production of Olanzapine, which will involve more simple and economical chemical steps, while allowing obtaining high yields of the final product having high purity by environment friendly process.

SUMMARY OF THE INVENTION

In accordance with one preferred embodiment, the present invention provides for an improved, environment friendly, industrially feasible and concise process for producing pure form of Olanzapine, by reacting 2-(2-aminoanilino)-5-methylthiophene-3-carbonitrile with N-methyl piperazine in conjunction with N-methyl piperazine acid salt.

In accordance with another preferred embodiment, the present invention provides an improved environment friendly process for producing a pure form of Olanzapine, by reacting 2-(2-aminoanilino)-5-methylthiophene-3-carbonitrile with N-methyl piperazine in conjunction with N-methyl piperazine acid salt in a one step reaction without employing any solvent, at a temperature of 90-138° C., preferably 110-125° C., wherein the ratio of 2-(2-aminoanilino)-5-methylthiophene-3-carbonitrile and N-methyl piperazine is more than 1:4 weight by volume.

In accordance with another embodiment, the present invention provides for an improved, industrially feasible and concise process for producing pure form of Olanzapine, by reacting 2-(2-aminoanilino)-5-methylthiophene-3-carbonitrile with N-methyl piperazine in conjunction with N-methyl piperazine acid salt in presence of a solvent. The solvent can be selected from toluene, dimethylsulfoxide, n-butanol, methyl ethyl ketone, dimethyl formamide, or a mixture thereof.

In accordance with another preferred embodiment, the present invention provides an improved process for producing Olanzapine by condensing 4-amino-2-methyl-10H-thieno[2,3-b][1,5]benzodiazepine or its hydrochloride salt with N-methyl piperazine at 90 to 138° C. without employing any solvent, wherein the ratio of 4-amino-2-methyl-10H-thieno[2,3-b][1,5]benzodiazepine and N-methyl piperazine is more than 1:4 weight by volume. It is surprisingly found that the absence of solvents lead to reduction in reaction time to 2-3 hours, as compared to 20 hours reported in prior art.

In accordance with another preferred embodiment the N-methylpiperazine acid salt is prepared in situ in the reaction mass or prepared separately and added to the reaction mass.

In accordance with still another embodiment, the present invention provides an improved process for obtaining a polymorphic Form I of Olanzapine by producing the crude Olanzapine according to the above-mentioned processes and crystallizing the same in a mixture of two or more solvents, wherein the solvents are selected from a group comprising acetonitrile, dichloromethane, diisopropylether, cyclohexane, hexane, t-butyl methyl ether and propionitrile.

In accordance with still another embodiment, the present invention provides an improved process for obtaining a polymorphic Form I of Olanzapine by producing the crude Olanzapine according to the above-mentioned process and crystallizing the same in a mixture of dichloromethane and diisopropylether or cyclohexane.

In accordance with still another embodiment, the present invention provides an improved process for obtaining a polymorphic Form I of Olanzapine by producing the crude Olanzapine according to the above-mentioned process and crystallizing the same in a mixture of dichloromethane and acetonitrile.

DETAILED DESCRIPTION OF THE INVENTION

According to the preferred embodiments of the invention, there is provided a pure form of 2-methyl-4-(4-methyl-1-piperazinyl)-10H-thieno[2,3-b]1,5-benzodiazeine[1], commonly known as Olanzapine by an improved process.

Reaction Scheme:

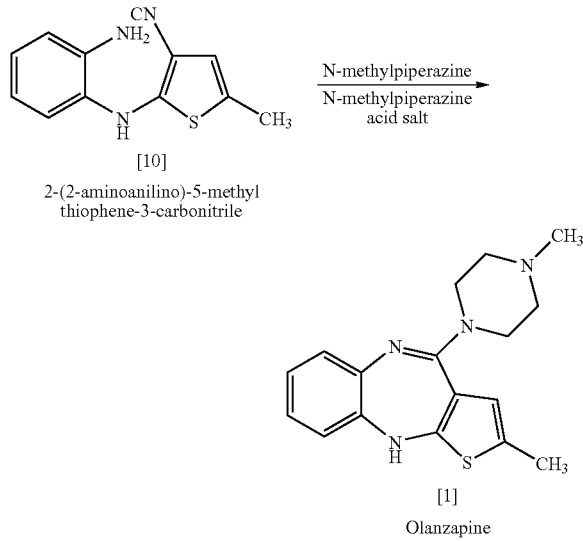

2-(2-aminoanilino)-5-methyl thiophene-3-carbonitrile

Olanzapine

The process disclosed herein comprises reaction of 2-(2-aminoanilino)-5-methylthiophene-3-carbonitrile [10] with N-methylpiperazine in conjunction with N-methyl piperazine acid salt to give Olanzapine. The reaction is carried out at 90-138° C., preferably at 110-125° C. in 6-12 hours.

The process disclosed in the present invention is performed without employing additional solvent, which leads to a less cumbersome workup, which is more suitable for large-scale manufacturing of pure Olanzapine. Further the absence of solvents saves the cost in terms of raw material, since recovery of the solvent is not needed therefore utility costs are also saved. The process is environment friendly, as the vapors of solvents are not spread in the atmosphere.

N-Methylpiperazine acid salt can be prepared in situ or can be prepared separately and then added into the reaction mixture. N-Methylpiperazine acid salt is prepared by the reaction of N-methylpiperazine with an acid in usual fashion. The acid used to prepare N-methylpiperazine acid salt can be chosen from organic or inorganic acids. The preferred organic acids can be formic acid, substituted or unsubstituted acetic acid e.g. acetic acid or trifluoroacetic acid, alkyl, aryl or aralkyl sulphonic acid e.g. methane sulphonic acid, p-toluene sulphonic acid, substituted or unsubstituted benzoic acid, etc. The preferred inorganic acids are phosphoric acid, hydro halide acid e.g. hydrochloric acid, sulfuric acid, perchloric acid and lewis acids such as aluminium chloride.

The solvent does not play any role in the reaction and reaction proceeds well in absence of any solvent, but alternatively the reaction can be performed in presence of a solvent.

The solvent can be selected from toluene, dimethylsulfoxide, n-butanol, methyl ethyl ketone, dimethyl formamide, or a mixture thereof.

After the completion of reaction, water miscible or water immiscible solvent is added followed by the addition of water. In case of water miscible solvents addition of water forms crude olanzapine directly, whereas in case of water immiscible solvent, solvent is removed to obtain crude Olanzapine. This crude Olanzapine is dried at ambient temperature and crystallized in different solvents or solvent systems to obtain different crystallized forms of Olanzapine, as desired. The solvent used for the work up can be selected from chlorinated solvent, amidic solvent, ketonic solvent, ethereal solvent, ester solvent etc. Few examples, but not limited are dimethylformamide, tetrahydrofuran, dioxane, acetone, acetonitrile, ethyl acetate or dichloromethane.

Figure 1:
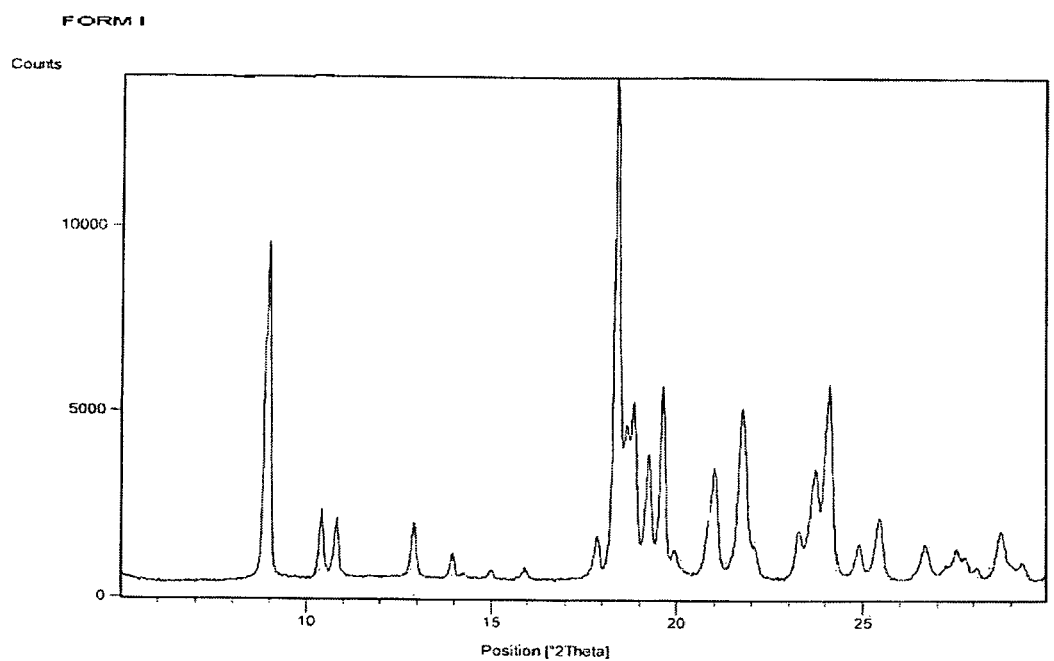
FIG. 1: XRD pattern of Polymorphic Form I of Olanzapine.

Stable Form I is prepared from the crude Olanzapine by crystallizing, essentially in a mixture of two or more solvents, selected from a group comprising acetonitrile, dichloromethane, diisopropylether, cyclohexane, hexane, t-butyl methyl ether and propionitrile, in high yield and high purity (>99.6%). Crude Olanzapine is taken first into solvent mixture and then 30-50% (v/v) of the solvent is distilled out, the reaction mass is cooled and filtered. The crystallized Form I is obtained which is highly pure and stable. Its XRD pattern is given in FIG. 1.

Figure 2:
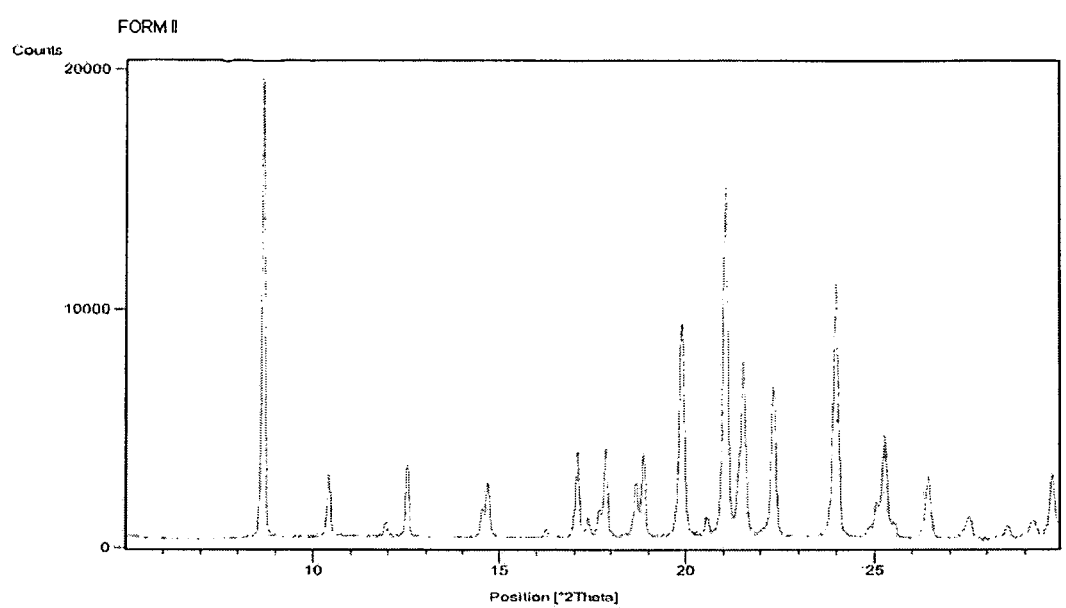
FIG. 2: XRD pattern of Polymorphic Form II of Olanzapine.

Polymorph Form II can be prepared from crude Olanzapine by dissolving it in acetonitrile and/or other solvents known in the prior art at 75-77° C., and cooling to 0-5° C. in high yield and high purity (>99.6%). Its XRD pattern is given in FIG. 2.

The other polymorphic forms of Olanzapine as mentioned in the prior arts like form III, IV, V can be prepared from the crude Olanzapine.

The compound 2-(2-aminoanilino)-5-methylthiophene-3-carbonitrile, the key intermediate, is obtained by the hydrogenation of 2-(2-nitroanilino)-5-methylthiophene-3-carbonitrile in presence of aprotic and/or protic solvents. The hydrogenation is done over metal carbon e.g. Pd/C or Pt/C. The most preferred metal is palladium. The preferred reaction temperature is 45-60° C.

In the prior art, the hydrogenation of 2-(2-nitroanilino)-5-methylthiophene-3-carbonitrile is carried out by employing stannous chloride and hydrogen chloride in aqueous ethanol. Stannous chloride generates effluents, which is environmentally hazardous. Another problem of using metal chloride is that it results in high sulphated ash content in the final product. However present invention provides a mild process that helps in removing all these drawbacks.

2-(2-nitroanilino)-5-methylthiophene-3-carbonitrile in turn is prepared from 2-amino-5-methylthiophene-3-carbonitrile with ortho halonitrobenzene in presence of base for example potassium hydroxide, in a solvent such as acetonitrile at low temperature preferably below room temperature more preferably at 0-10° C.

According to another aspect of the invention and in line with the above discussion, there is also provided a process for the preparation of pure Olanzapine of Formula 1 or an acid addition salt thereof, which comprises reaction of 4-amino-2-methyl-10H-thieno[2,3-b][1,5]benzodiazepine hydrochloride (3) with N-methyl piperazine essentially in absence of any solvent at a temperature of 90-138° C.

It is surprisingly found that absence of the solvent in this case leads to reduction in reaction time to 2-3 hours from 20 hours. The reduction in reaction time reduces the formation of impurities e.g. dimer of Olanzapine [11].

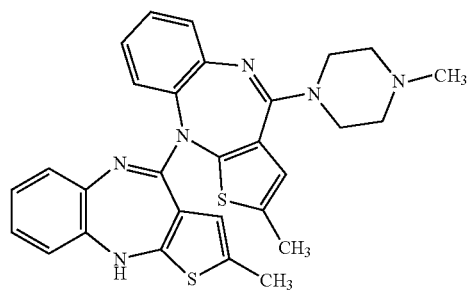

[11]

The compound 4-amino-2-methyl-10H-thieno[2,3-b]1,5] benzodiazepine hydrochloride is obtained from 2-(2-aminoanilino)-5-methylthiophene-3-carbonitrile by cyclization of the later compound in presence of an alcoholic solvent, preferably isopropyl alcohol in mild acidic conditions at a temperature, which is more than the room temperature.

For the purpose of promoting a further understanding of the present invention and its preferred features and embodiments, the following examples are being provided. It will be understood, however, that these examples are illustrative, and not limiting in nature.

EXAMPLE 1

Preparation of 2-Amino-5-methylthiophene-3-carbonitrile

A mixture of (46.2 g) of sulphur, propionaldehyde (100 g) and dimethylformamide (200 ml) are taken under nitrogen. Triethylamine (113.2 ml) is added at 5° C. A solution of malonitrile (95.2 g) in dimethylformamide (200 ml) is added. After addition, the reaction mixture is stirred for 45 minutes. The reaction mixture is then poured onto ice water (2400 ml). The solid thus obtained is isolated by filtration, washed with chilled water and dried to obtain the title compound (139.5 g).

EXAMPLE 2

Preparation of 2-(2-Nitroanilino)-5-methylthiophene-3-carbonitrile

Potassium hydroxide (101.4 g) in acetonitrile (150 ml) is taken under nitrogen and cooled to 0-5° C. A solution of 2-amino-5-methylthiophene-3-carbonitrile (100 g) and o-fluoronitrobenzene (122.6 g) in acetonitrile (550 ml) is added. The reaction is then stirred for 3 hours and chilled water is added. The solid thus obtained is filtered off and air-dried. The solid is crystallized from water-methanol mixture and the crystallized solid is dried under vacuum at 40-45° C. to obtain the title compound (140 g).

EXAMPLE 3

Preparation of 2-(2-aminoanilino)-5-methylthiophene-3-carbonitrile 2-(2-Nitroanilino)-5-methylthiophene-3-carbonitrile (100 g) is taken in ethyl acetate (1000 ml). The reaction mixture is then hydrogenated by 5% Pd/C (15 g) at 50-55° C. at 10-12 Kg pressure. The reaction mixture is filtered, and ethyl acetate is distilled off to get the title compound.

EXAMPLE 4

Preparation of 2-methyl-4-(4-methyl-1-piperazinyl)-10H-thieno-[2,3-b][1,5]benzodiazepine 2-(2-Aminoanilino)-5-methylthiophene-3-carbonitrile (2.0 g) is taken in N-methyl-piperazine (12 ml) and N-methyl piperazine.HCl (4.6 g). The solution is heated at 120° C. until completion of reaction. The reaction mass is cooled to 70-75° C. and acetone and activated charcoal are added. The reaction mixture is stirred for 30 minutes and filtered. The water is added at 45-50° C., the mixture is cooled up to room temperature and the precipitated solid is filtered off and washed with acetone-water mixture.

EXAMPLE 5

Preparation of 2-methyl-4-(4-methyl-1-piperazinyl)-10H-thieno-[2,3-b][1,5]benzodiazepine 2-(2-Aminoanilino)-5-methylthiophene-3-carbonitrile (2.0 g) is taken in N-methyl-piperazine (12 ml) and acetic acid (2 ml). The solution is heated at 120° C. until completion of reaction. The reaction mass is cooled and tetrahydrofuran is added. The reaction mixture is stirred for 30 minutes. The water is added at 45-50° C., the mixture is cooled up to room temperature and the solid is precipitated out. The solid is filtered off and washed with tetrahydrofuran-water mixture.

EXAMPLE 6

Preparation of 2-methyl-4-(4-methyl-1-piperazinyl)-10H-thieno-[2,3-b][1,5]benzodiazepine 2-(2-Aminoanilino)-5-methylthiophene-3-carbonitrile (10.0 g) is taken in N-methyl-piperazine (60 ml) and N-methyl-piperazine hydrochloride (24 gm). The solution is heated at 120° C. until completion of reaction. The reaction mass is cooled and dichloromethane (100 ml) and water is added. The mixture is cooled up to room temperature and dichloromethane layer is separated. 50 ml dichloromethane is evaporated and cyclohexane is added in clear solution. On Cooling the solution, solid is separated out, which is filtered and dried under vacuum to get Olanzapine Form I. (Purity >99.6%)

EXAMPLE 7

Preparation of Polymorph Form I

The crude Olanzapine solid [1] is dissolved in a mixture of dichloromethane (5 times) and Diisopropylether or cyclohexane (5 times). Crystallized solid obtained is filtered and dried under vacuum at 45-50° C. to give Form I. (Purity >99.6%)

EXAMPLE 8

Preparation of Polymorph Form II

The crude Olanzapine solid is dissolved in acetonitrile at 75-77° C. and then cooled to 0-5° C., and solid obtained is filtered and dried under vacuum at 50-55° C. to give Form II. (Purity >99.6%)

EXAMPLE 9

Preparation of 4-amino-2-methyl-10H-thieno[2,3-b][1,5] benzodiazepine hydrochloride 2-(2-Nitroanilino)-5-methylthiophene-3-carbonitrile (100 g) is taken in ethyl acetate (1000 ml). 5% Pd/C (15 g) is added and hydrogenated at 50° C. for 15 hours. Ethyl acetate is distilled off to get the solid. The solid is taken in isopropyl alcohol (500 ml), concentrated hydrochloric acid (102 ml) is added at room temperature and the mixture is heated up to 80-82° C. for 12 hours under stirring. The solution is cooled to precipitate the solid, filtered and dried under vacuum at 55-60° C. to give the title compound (80 g).

EXAMPLE 10

Preparation of 2-methyl-4-(4-methyl-1-piperazinyl)-10H-thieno-[2,3-b][1,5]benzodiazepine 4-Amino-2-methyl-10H-thieno[2,3-b][1,5] benzodiazepine hydrochloride (100 g) is taken in N-methyl piperazine (500 ml). Reaction mixture is heated at 120° C. for 3 hours. The reaction mass is cooled and acetonitrile (400 ml) is added under stirring for 30 minutes. Water (500 ml) is added and the mixture is cooled up to room temperature and stirred to precipitate the solid. The solid is filtered off, washed with acetonitrile (100 ml) and dried at ambient temperature to obtain the crude title compound (64 g).

We claim:

1. A process for producing 2-methyl-4-(4-methyl-1-piperazinyl)-10H-thieno[2,3-b][1,5] benzodiazepine, the process comprising condensing 4-amino-2-methyl-10H-thieno[2,3-b][1,5]benzodiazepine or a salt thereof with N-methyl piperazine to produce 2-methyl-4-(4-methyl-1-piperazinyl)-10H-thieno[2,3-b][1,5]benzodiazepine, wherein the process is carried out in the absence of a solvent for 2-3 hours at a reaction temperature of 110° C.-125° C.

2. The process according to claim 1, wherein the ratio of 4-amino-2-methyl-10H-thieno[2,3-b][1,5]benzodiazepine and N-methyl piperazine is more than 1:4 weight by volume.

3. The process according to claim 1, wherein said salt is a hydrochloride salt of 4-amino-2-methyl-10H-thieno[2,3-b][1,5]benzodiazepine.

4. The process according to claim 1, further comprising the step of adding (i) water and (ii) a water miscible or water immiscible solvent to obtain solid 2-methyl-4-(4-methyl-1-piperazinyl)-10H-thieno[2,3-b][1,5] benzodiazepine.

5. The process according to claim 4, wherein the water miscible and immiscible solvent is selected from dimethylformamide, tetrahydrofuran, dioxane, acetone, acetonitrile, ethyl acetate and dichloromethane.

* * * * *